United States Patent [19]

Langhauser et al.

[11] Patent Number: 5,621,127
[45] Date of Patent: Apr. 15, 1997

[54] PREPARATION OF BRIDGED HALF SANDWICH COMPLEXES

[75] Inventors: Franz Langhauser, Bad Dürkheim; Hans-Joachim Müller, Grünstadt; Jürgen Kerth, Carlsberg; Günther Schweier, Friedelsheim; Bernhard Rieger, Nehren, all of Germany

[73] Assignee: BASF Aktiengesellschaft, Ludwigshafen, Germany

[21] Appl. No.: 435,447

[22] Filed: May 5, 1995

[30] Foreign Application Priority Data

May 13, 1994 [DE] Germany .......................... 44 16 876.4

[51] Int. Cl.$^6$ .............................. C07F 17/00; C07F 7/28
[52] U.S. Cl. ................ 556/11; 556/52; 556/43; 534/15
[58] Field of Search ................... 556/11, 52, 56, 556/43; 534/15

[56] References Cited

U.S. PATENT DOCUMENTS 5,055,438  10/1991  Canich .................................. 502/117

FOREIGN PATENT DOCUMENTS

62039/90  1/1994  Australia .
416815    3/1991  European Pat. Off. .

Primary Examiner—Porfirio Nazario-Gonzalez
Assistant Examiner—Jean F. Vollano
Attorney, Agent, or Firm—Keil & Weinkauf

[57] ABSTRACT

Bridged half sandwich complexes are prepared by reacting cyclopentadienides with aziridines and subsequently adding metallating agents and transition metal compounds.

3 Claims, No Drawings

PREPARATION OF BRIDGED HALF SANDWICH COMPLEXES

The present invention relates to processes for preparing bridged half sandwich complexes.

Bridged half sandwich complexes are suitable as catalysts for the preparation of polyolefins.

EP-A 416 815 and U.S. Pat. No. 5,055,438 describe bridged half sandwich complexes and processes for their preparation. In these processes, initially cyclopentadienides are prepared and isolated. These salts are then added as solid or suspension slowly to a solution of dimethylchlorosilane in THF. Subsequently the resulting chlorosilane is converted in aliphatics to the required ligand. The metering of this very air-sensitive Li salt is preparatively very demanding, and the yields of ligand are often unsatisfactory.

It is an object of the present invention to provide a process for preparing bridged half sandwich complexes which makes it possible to obtain bridged half sandwich complexes in a more efficient (ie. with better yield) and preparatively simpler manner than in the prior art.

We have found that is object is achieved by a process for preparing bridged half sandwich complexes of the formula I

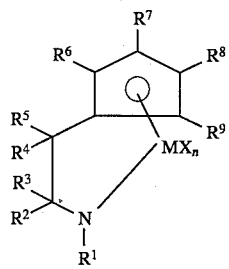

where
M is a metal of Group IVb or Vb of the Periodic Table or a metal from the lanthanide group,
X is halogen, hydrogen, $C_1$–$C_{10}$-alkyl, $C_3$–$C_{10}$-cycloalkyl, $C_6$–$C_{15}$-aryl, alkylaryl having 7 to 15 carbon atoms or -$OR^{10}$,
where
$R^{10}$ is $C_1$–$C_{10}$-alkyl, $C_6$–$C_{15}$-aryl, alkylaryl, arylalkyl, fluoroalkyl or fluoroaryl having in each case 1 to 10 carbon atoms in the alkyl radical and 6 to 20 carbon atoms in the aryl radical,
n is the valency of M minus two,
$R^1$ is hydrogen, $C_1$–$C_{10}$-alkyl, $C_3$–$C_{10}$-cycloalkyl which in turn can carry $C_1$–$C_{10}$-alkyl groups as substituents, or $C_6$–$C_{15}$-aryl or arylalkyl having 1 to 10 carbon atoms in the alkyl radical and 6 to 20 carbon atoms in the aryl radical or $Si(R^{11})_3$,
where
$R^{11}$ is $C_1$–$C_{10}$-alkyl, $C_6$–$C_{15}$-aryl or $C_3$–$C_{10}$-cycloalkyl,
$R^2$ to $R^9$ are each hydrogen, $C_1$–$C_{10}$-alkyl, $C_3$–$C_{10}$-cycloalkyl, which in turn can carry $C_1$–$C_{10}$-alkyl groups as substituents, or $C_6$–$C_{15}$-aryl or arylalkyl having 1 to 10 carbon atoms in the alkyl radical and 6 to 20 carbon atoms in the aryl radical, it also being possible for two adjacent radicals together to be cyclic groups having 4 to 15 carbon atoms, or $Si(R^{12})_3$,
where
$R^{12}$ is $C_1$–$C_{10}$-alkyl, $C_6$–$C_{15}$-aryl or $C_3$–$C_{10}$-cycloalkyl,
which comprises in a first step reacting cyclopentadienides of the formula II

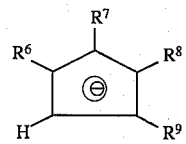

with aziridines of the general formula III

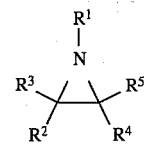

to give ligand systems of the general formula IV

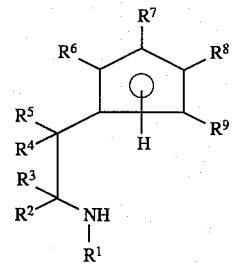

and subsequently reacting the ligand systems of the formula IV with metallating agents and $MX_{n+2}$.

The process according to the invention is preferably used to prepare bridged half sandwich complexes of the general formula I where
M is a metal of Group IVb of the Periodic Table, in particular titanium, zirconium or hafnium,
X is chlorine or methyl,
$R^1$ is $C_6$–$C_{15}$-aryl, in particular phenyl,
$R^2$ to $R^9$ are each hydrogen, $C_1$–$C_4$-alkyl or two adjacent radicals such as $R^2$ and $R^3$, $R^3$ and $R^4$, $R^4$ and $R^5$ or $R^6$ and $R^7$, $R^7$ and $R^8$, $R^8$ and $R^9$ are groups having 4 to 15 carbon atoms, preferably 4 to 12 carbon atoms.

Examples of particularly preferred bridged half sandwich complexes include
(tert-butylamido)(tetramethyl-$\eta^5$-cyclopentadienyl)ethylenezirconium dichloride
(methylamido)($\eta^5$-cyclopentadienyl)ethylenezirconium dichloride
(phenylamido)($\eta^5$-cyclopentadienyl)ethylenezirconium dichloride
(phenylamido)($\eta^5$-cyclopentadienyl)-1,2-dimethylethylenezirconium dichloride
(phenylamido)(tetramethyl-$\eta^5$-cyclopentadienyl)-1,2-dimethylethylenezirconium dichloride
(tert-butylamido)(tetramethyl-$\eta^5$-cyclopentadienyl)ethylenetitanium dichloride
(phenylamido)($\eta^5$-fluorenyl)ethylenezirconium dichloride
(phenylamido)($\eta^5$-indenyl)ethylenezirconium dichloride.

In the process according to the invention the first step entails reaction of cyclopentadienides of the formula II

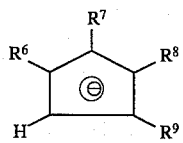

with aziridines of the formula III

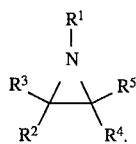

Concerning preferred substituents, reference may be made to the above statements.

The cyclopentadienides II can be used in the form of alkali metal cyclopentadienides, preferably as lithium compounds, as are also commercially available (for example cyclopentadienyllithium from Fluka).

The aziridines III can be prepared as described by D. A. Evans, M. M. Faul, M. T. Bilodeau, J. Org. Chem., 56 (1991) 6744–6746.

The reaction of the cyclopentadienides II with the aziridines III takes place under an inert gas atmosphere. It is preferable to introduce the aziridines first, in particular in an organic solvent such as ethers, and then to add the cyclopentadienides II at temperatures in the range from −70° C. to 0° C., in particular to −10° C. The ratio of the amounts of II and III is in the range from 1:3 to 3:1, preferably 2:1 to 1:2. The mixture is then heated to temperatures in the range from 10° to 60° C., preferably 20° to 40° C., and allowed to react for 2 to 18 hours, preferably 6 to 15 hours. For working up the mixture, aqueous solutions of ammonium salts, preferably a saturated ammonium chloride solution are added and the resulting ligand system IV is separated of.

Mixtures of diastereomers of aziridine III can be used or to prepare enantiomerically pure complexes I, enantiomerically pure compounds can be used.

The ligand systems IV can be in the form of a mixture of isomers or in the form of a pure isomer.

The ligand systems IV can then be mixed with metallating agents such as alkali metal or alkaline earth metal alkyl or hydrides, preferably n-butyllithium. This is preferably done by mixing the ligand systems IV with organic solvents such as hydrocarbons and adding, at temperatures from −10° to 50° C., in particular 15° to 35° C., the metallating agents. The metallating agents are preferably also mixed with an organic solvent such as hydrocarbons. The ratios of the amounts of IV to the metallating agents are in the range from 1:10 to 10:1, in particular 1:5 to 5:1. The reaction mixture is then heated to temperatures in the range from 30° to 120° C., preferably 60° to 80° C., and the resulting metallated ligand system is separated off.

The reaction with $MX_{n+2}$ is preferably carried out by mixing $MX_{n+2}$ or a complex of $MX_{n+2}$ with an inert solvent, for example ethers, with a solvent such as toluene, and adding the metallated ligand system at temperatures from −80° to 0° C., in particular −60° to 20° C. The ratios of the amounts of $MX_{n+2}$ to the metallated ligand system are in the range from 2:1 to 1:2, preferably 1.5:1 to 1:1.5.

After the addition is complete, the mixture is heated to 10° to 50° C., preferably 20° to 30° C., and left to react for 0.1 to 10 days, preferably 2 to 5 days. The resulting bridged half sandwich complex I is subsequently separated off.

The process according to the invention is distinguished by its efficiency and by its preparative simplicity, and the resulting bridged half sandwich complexes are suitable as catalysts for preparing polyolefins.

EXAMPLE 1

Preparation of (phenylamido)(η⁵-cyclopentadienyl)ethylenezirconium dichloride I1

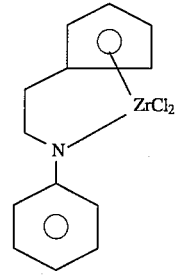

a) Reaction of cyclopentadienyllithium II1 with N-phenylaziridine III1 to give N-(2-cyclopentadienylethyl)aniline IV1

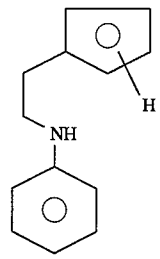

0.36 g (5 mmol) of cyclopentadienyllithium was added in several portions to a solution of 0.6 g (=5 mmol) of N-phenylaziridine in 50 ml of tetrahydrofuran (THF) under an argon atmosphere at −30° C. After the addition was complete, the mixture was stirred at −30° C. for 1 hour and then warmed to room temperature over the course of 12 hours. Then 50 ml of a saturated aqueous NH₄Cl solution were added, the mixture was stirred for 1 hour and the organic phase was separated off. The latter was dried over anhydrous Na₂SO₄ and filtered, and the solvent was removed under oil pump vacuum. 0.83 g (4.5 mmol, 90% of theory) of IV1 was obtained as a yellow oil.

Elemental analysis: calculated 84.28 C 8.16 H 7.56 N found 84.11C 8.20 H 7.44 N b) Reaction of IV1 with n-butyllithium 5.6 ml (9 mmol) of a 1.6 molar solution of n-butyllithium in hexane were added to a solution of 0.83 g (4.5 mmol) of IV1 in 70 ml of pentane under an argon atmosphere at room temperature and, after the addition was complete, the mixture was stirred at room temperature for 3 hours. It was subsequently refluxed for 1 hour and cooled to −30° C., and the white precipitate was filtered off and dried under oil pump vacuum. 0.83 g (4.2 mmol, 93% of theory) of metallated ligand system was obtained.

c) Reaction of the metallated ligand system with ZrCl₄

0.83 g (4.2 mmol) of the metallated ligand system prepared in b) was added in several portions to a suspension, cooled to −30° C., of 0.8 g (2.1 mmol) of ZrCl₄×2 THF in 100 ml of toluene. After the addition was complete, the mixture was warmed to room temperature and stirred for 3 days. It was subsequently filtered, the precipitate was washed three times with 50 ml of toluene each time and evaporated to dryness under oil pump vacuum. The remaining residue was taken up in 40 ml of methylene chloride and crystallized at −78° C. 0.35 g (1 mmol, 48% of theory) of I1 was obtained as orange-red microcrystalline powder.

Elemental analysis: calculated 45.21 C 3.79 H 4.06 N 26.41Zr found 45.00 C 3.90 H 4.02 N −26.20 Zr

We claim:

1. A process for preparing bridged half sandwich complexes of the formula I

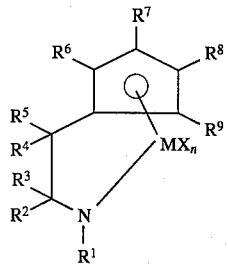

where

M is a metal of Group IVb or Vb of the Periodic Table or a metal from the lanthanide group, X is halogen, hydrogen, $C_1$–$C_{10}$-alkyl, $C_3$–$C_{10}$-cycloalkyl, $C_6$–$C_{15}$-aryl, alkylaryl having 7 to 15 carbon atoms or $-OR^{10}$, where $R^{10}$ is $C_1$–$C_{10}$-alkyl, $C_6$–$C_{15}$-aryl, alkylaryl, arylalkyl, fluoroalkyl or fluoroaryl having in each case 1 to 10 carbon atoms in the alkyl radical and 6 to 20 carbon atoms in the aryl radical, n is the valency of M minus two, $R^1$ is hydrogen, $C_1$–$C_{10}$-alkyl, $C_3$–$C_{10}$-cycloalkyl which in turn can carry $C_1$–$C_{10}$-alkyl groups as substituents, or $C_6$–$C_{15}$-aryl or arylalkyl having 1 to 10 carbon atoms in the alkyl radical and 6 to 20 carbon atoms in the aryl radical or $Si(R^{11})_3$, where $R^{11}$ is $C_1$–$C_{10}$-alkyl, $C_6$–$C_{15}$-aryl or $C_3$–$C_{10}$-cycloalkyl, $R^2$ to $R^9$ are each hydrogen, $C_1$–$C_{10}$-alkyl, $C_3$–$C_{10}$-cycloalkyl, which in turn can carry $C_1$–$C_{10}$-alkyl groups as substituents, or $C_6$–$C_{15}$-aryl or arylalkyl having 1 to 10 carbon atoms in the alkyl radical and 6 to 20 carbon atoms in the aryl radical, it also being possible for two adjacent radicals together to be cyclic groups having 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, which comprises in a first step reacting cyclopentadienides of the formula II

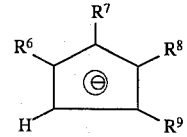

with aziridines of the formula III

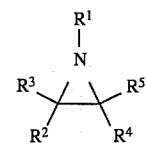

to give ligand systems of the formula IV

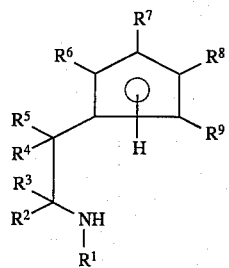

and subsequently reacting the ligand systems of the formula IV with metallating agents and $MX_{n+2}$.

2. A process as claimed in claim 1, wherein M is a metal of group IVb of the Periodic Table.

3. A process as claimed in claim 1, wherein $R^1$ is $C_6$–$C_{15}$-aryl.

* * * * *